United States Patent [19]

Gregoris

[11] Patent Number: 5,500,530
[45] Date of Patent: Mar. 19, 1996

[54] ELECTRO-OPTIC ICE DETECTION

[75] Inventor: Dennis J. Gregoris, Etobicoke, Canada

[73] Assignee: SPAR Aerospace Limited, Brampton, Canada

[21] Appl. No.: 332,100

[22] Filed: Oct. 31, 1994

[51] Int. Cl.⁶ .................................................. G01N 21/35
[52] U.S. Cl. ................... 250/339.11; 250/339.12; 250/341.8; 244/134 F; 340/583
[58] Field of Search ................ 250/339.12, 339.1, 250/339.11, 341.8; 244/134 F; 340/583

[56] References Cited

U.S. PATENT DOCUMENTS 4,808,824  2/1989  Sinnar .................................. 250/339.1
5,180,122  1/1993  Christian et al. ..................... 244/134 F
5,218,206  6/1993  Schmitt et al. ...................... 250/339.1

Primary Examiner—Carolyn E. Fields

[57] ABSTRACT

To determine whether ice is present on an aircraft wing, the intensity of light in a band between 1.16 and 1.20 microns is determined as is the intensity in a band between 1.24 and 1.28 microns. The contrast, defined as the difference between the intensities over the sum of these intensities, is determined. Because of the peculiar characteristics of the reflectivity of ice, water, Type I de-icing fluid, and Type II anti-icing fluid, if the contrast is positive, it is an indication of ice on the wing whereas if it is negative it is an indication there is no ice present.

24 Claims, 7 Drawing Sheets

ELECTRO-OPTIC ICE DETECTION

BACKGROUND OF THE INVENTION

1. Field of the Invention

This invention relates to a method and apparatus for indicating the presence of ice on a surface.

2. Description of the Related Art

Ice on the surface of an aircraft wing reduces aerodynamic performance and may, therefore, constitute a safety hazard.

One system for detecting ice on a wing surface is described in U.S. Pat. No. 5,180,122 to Christian issued Jan. 19, 1993. The system disclosed in Christian has a camera which receives the light reflected from an aircraft wing and passes the full spectrum to a video imager which outputs a blue video signal having an intensity dependent upon the intensity of the full spectrum. Another camera has a filter passing a narrow band of light centered about 1.8 microns. This filtered light is used to generate a green video signal. A third camera passes a narrow band of light centered about 1.6 microns and a red video signal is constructed from this filtered light. Christian considers that ice has a peak in its reflectance spectra at 1.8 microns and dips in its spectrum at 1.25, 1.6 and 2.0 microns. Christian suggests certain other substances on the wing do not have a reflectance spectra dip at 1.6 microns and, consequently, areas of the wing surface covered ice have a distinguishable colour on a video monitor driven with the composite video signal.

This invention seeks to provide an improved electro-optic ice detection apparatus.

SUMMARY OF THE INVENTION

According to the present invention, there is provided a method of indicating the presence of ice on a surface, comprising the following steps: detecting the intensity of reflected light from said surface at a first lower wavelength band, said lower band being within a band extending from about 1.1 microns to about 1.3 microns; detecting the intensity of reflected light from said surface at a second upper wavelength band having substantially the same bandwidth as said lower band, said upper band being within a band extending from about 1.16 microns to about 1.3 microns; and determining the presence or absence of ice on said surface based upon the intensity of reflected light at said first band and the intensity of reflected light at said second band.

According to another aspect of the present invention, there is provided apparatus for determining the presence of ice on a surface, comprising the following: bandpass filter means configured to pass light within a first lower wavelength band, said lower band being within a band extending from about 1.1 microns to about 1.3 microns and within a second upper wavelength band having substantially the same bandwidth as said lower band, said upper band being within a band extending from about 1.16 microns to about 1.3 microns, said bandpass filter means for receiving light reflected from said surface; means for detecting the intensity of light passed through said bandpass filter means; and means responsive to said detecting means for determining the presence or absence of ice on said surface.

BRIEF DESCRIPTION OF THE DRAWINGS

In the drawings which illustrate example embodiments of the invention.

DETAILED DESCRIPTION OF THE PREFERRED EMBODIMENTS

Figure 1:
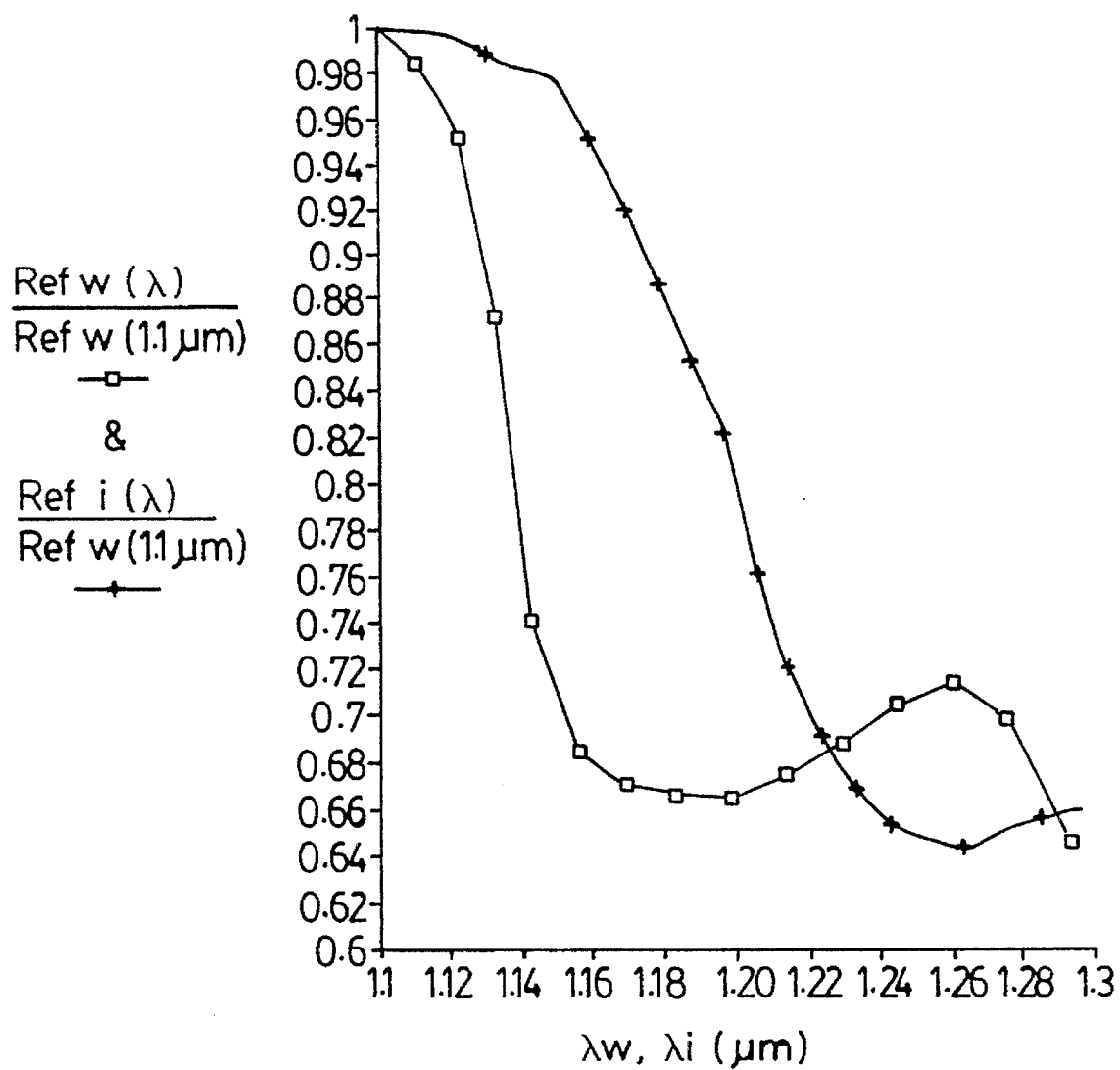
FIG. 1 is a graph of the effective spectral reflectivity of ice and water over a particular range of wavelengths.

It is well recognized that the reflectance of a substance varies with wavelength. I have discovered, however, that there is a certain wavelength band over which the reflectance spectra of ice and water are significantly different. This band extends from about 1.1 microns to about 1.3 microns. FIG. 1 is a graph of the reflectance of water ($Ref_w$) and ice ($Ref_i$), expressed as a fraction of the reflectance of water at 1.1 microns, over this wavelength band (for a 2 mm layer on a non-reflective surface given approximately normally incident light). The difference in the reflectance curves of water and ice over this band is readily apparent by reference to this figure. My discovery allows for a determination of whether a surface is covered with ice or water, as follows. A lower sub-band is chosen within the band of 1.1 to 1.3 microns and an upper sub-band is chosen within the band of 1.16 to 1.3 microns. These sub-bands are chosen such that they have the same bandwidth. Then, light reflected from a surface is analyzed to determine the intensity of the light in the lower band and in the upper band. The relative intensity in these two bands indicates whether the surface is covered with ice or with water.

For the foregoing method to be useful in determining whether ice is present on an aircraft surface, it must be effective even after an aircraft has been sprayed with Type I aircraft de-icing fluid and Type II aircraft anti-icing fluid. It has been found that Type I and Type II fluids have similar spectral reflectivity curves to that of water within the wavelength band of 1.1 to 1.3 microns. This similarity is believed to be the result of the fact that these fluids comprise glycol, di-ethylene or propylene glycols which have similar absorption properties to that of water, along with the fact that these fluids are usually diluted with water. At higher wavelengths, the reflectances of these fluids diverge from that of water and this is believed to be due to additives such as surfactants and plactisizing agents contributing different absorption bands. In the result, the subject method can distinguish ice from water, Type I, or Type II fluid. Furthermore, tests with a thin (approximately 1 mm) overlayer of water, Type I or Type II fluid on a 2 to 3 mm layer of ice show that such an overlayer has little effect on the ice signature in the 1.1 to 1.3 micron band. Thus, the subject method can detect ice even under a layer of water, Type I, or Type II fluid.

With reference to FIG. 1, I have also discovered that at any given wavelength between about 1.1 and 1.23 microns, light reflects from water with a lower intensity than it does from ice, whereas at any given wavelength from about 1.23 microns to about 1.3 microns, light reflects from water with a higher intensity than it does from ice. Furthermore, the reflectance of water from about 1.16 to 1.24 microns is lower than the reflectance of water from about 1.24 to 1.29 microns. These facts may be used as the basis for a robust method to determine whether or not a surface is covered with ice, as follows.

Firstly, a lower sub-band is chosen within the band of 1.16 to 1.24 microns and an upper sub-band is chosen within the band of 1.24 to 1.29 microns so that water has a lower reflectance in the lower sub-band than it does in the upper sub-band. Furthermore, each sub-band is chosen to have the same bandwidth. In order to maximize the difference between the reflectance spectra of ice and water, the preferred lower sub-band is from about 1.16 to 1.20 microns, where ice has a considerably greater reflectance than does water, and the preferred upper sub-band is between about 1.24 and 1.28 microns, where water has a considerably higher reflectance than does ice.

When light reflects from a surface covered with ice or water, the intensity of light within each of the chosen upper and lower sub-bands is calculated by integrating the reflectance across the lower band and across the upper band. The intensity in the lower band may be designated $R_L$ and in the upper band $R_U$. A quantity called the contrast, C, may then be calculated as follows:

$$C = \frac{R_L - R_U}{R_L + R_U}$$

If the contrast is positive, it is considered that ice is present on the surface. On the other hand, if the contrast is negative, it is considered that no ice is present.

By defining the contrast as a ratio of the difference between the two intensities over the sum, the contrast becomes a relative term such that the intensity of light impinging on the surface is of little importance.

As noted hereinbefore, the spectral reflectance of Type I and Type II fluids at the wavelengths of interest are similar to that of water such that the disclosed method may also distinguish ice from these fluids.

FIG. 1 shows the effective spectral reflectivity of ice and water independent of the effect of any underlying surface. An aircraft surface will contribute some reflectivity, but provided this additional reflectance is constant over the wavelengths of interest, it will not interfere with the determination of the presence of ice. Large aircraft are generally fabricated of aluminum. It has been found that the additional reflectance from an unpainted aluminum surface is approximately constant over the wavelengths of interest. The situation is different, however, where the aluminum is painted.

Figure 2:
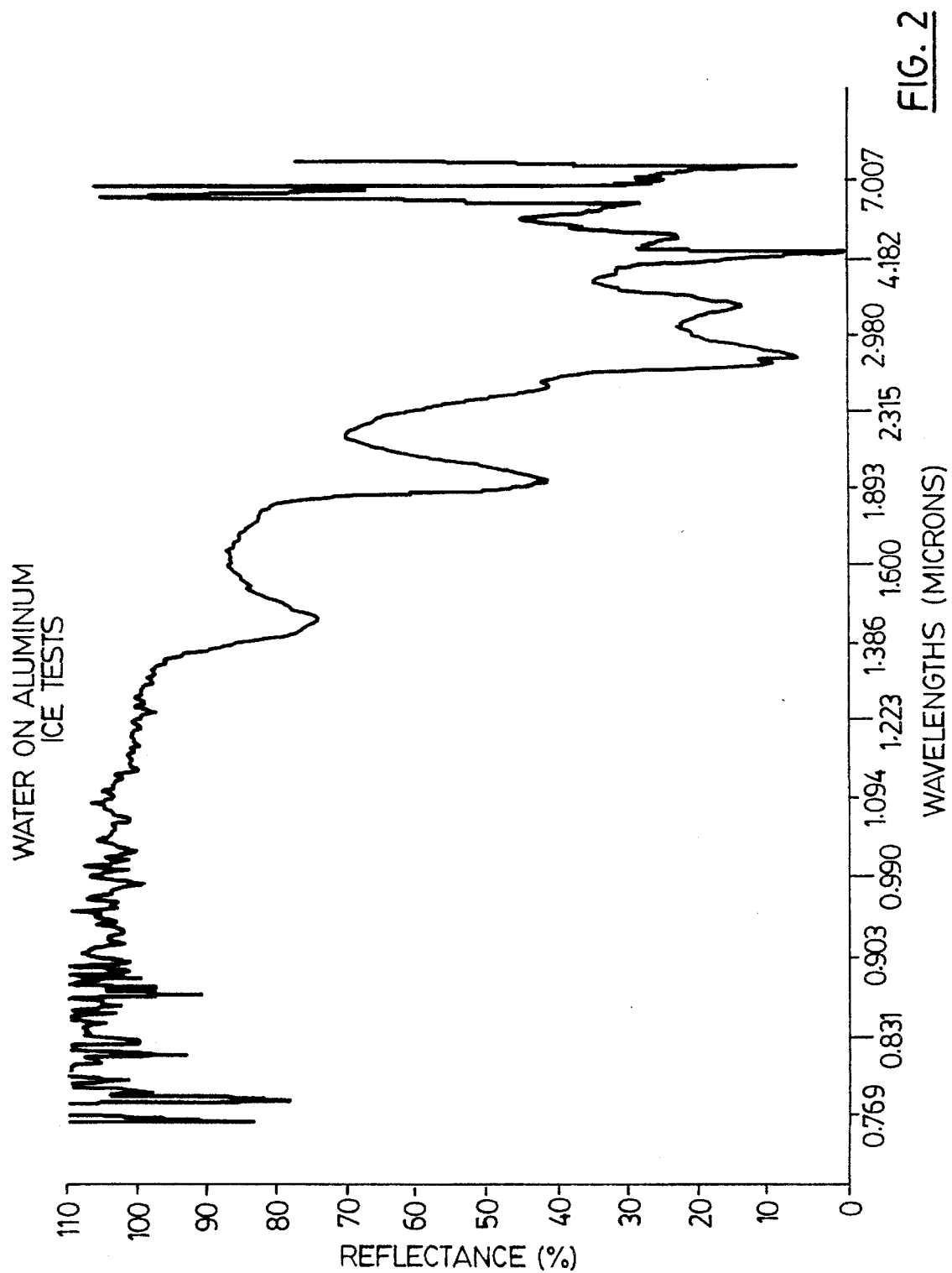
FIG. 2 is a graph of the reflectance spectrum of water on aluminum.
Figure 3:
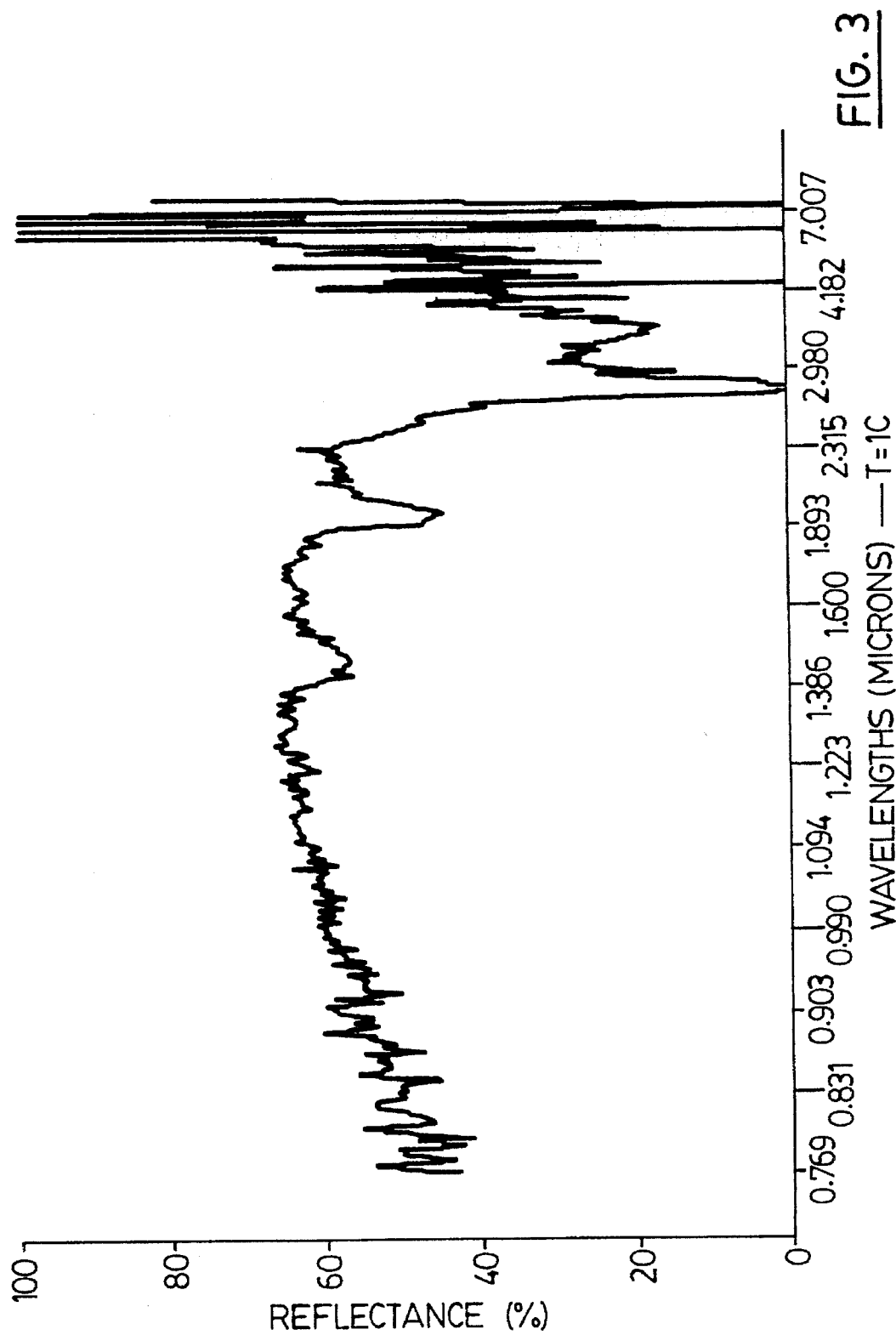
FIG. 3 is a graph of the reflectance spectrum of water on white painted aluminum.
Figure 4:
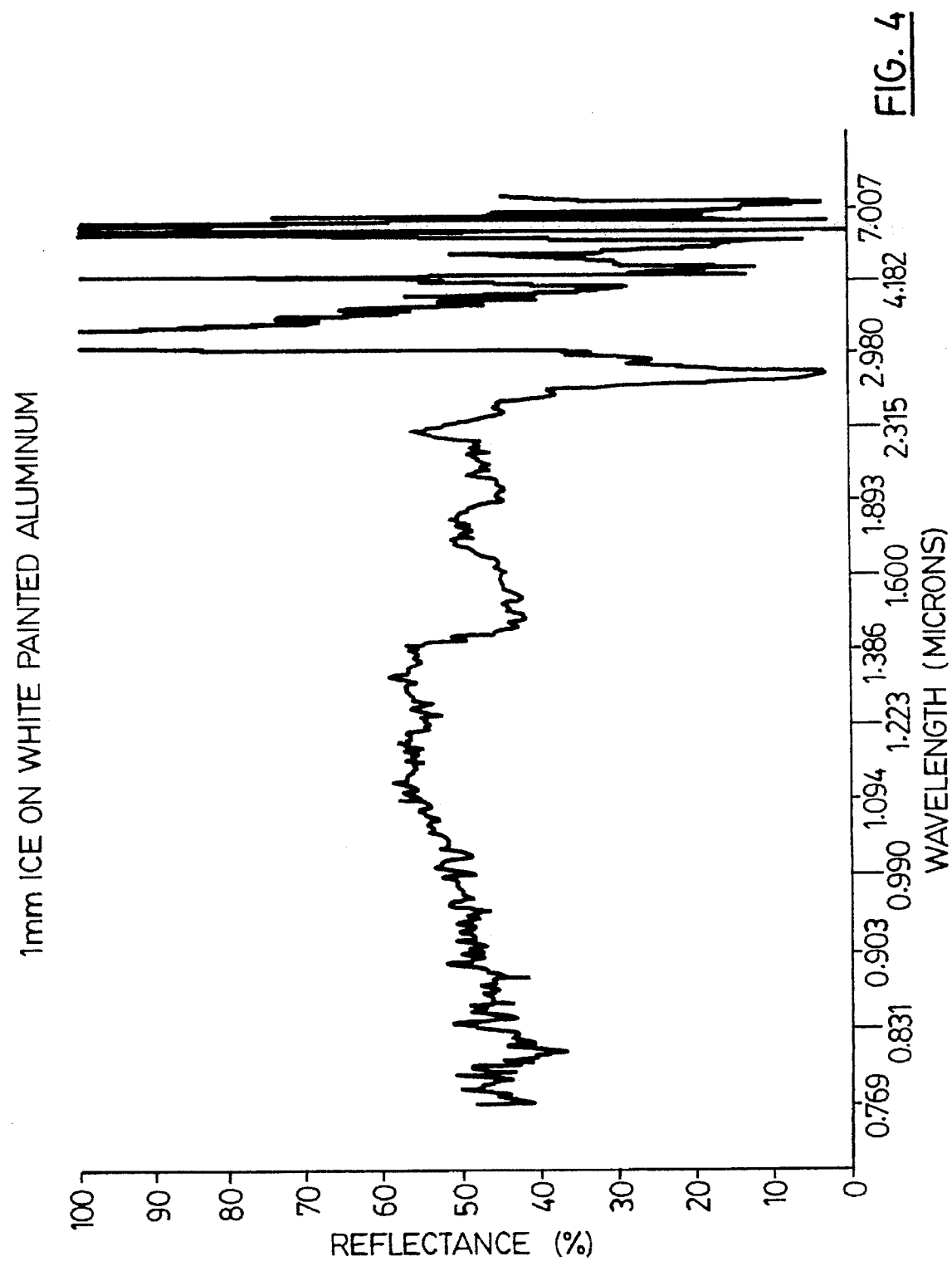
FIG. 4 is a graph of the reflectance spectrum of ice on white painted aluminum.

FIG. 2 shows the reflectance curve of water on aluminum over a broad wavelength spectrum. FIG. 3 shows the reflectance curve of water on white painted aluminum and FIG. 4 shows the reflectance curve of ice on white painted aluminum. The spectra for white painted surfaces were found to be essentially the same despite different surface finishes and substrate materials suggesting that the paint pigment material (titanium dioxide) is the dominant factor in the spectral signature. FIGS. 3 and 4 indicate an increase in reflectance with increasing wavelength for painted aluminum over the wavelengths of interest. To remove this effect, a reference band, with the same bandwidth as the upper band, is chosen such that, for an unpainted aluminum surface, the reflectance in the reference band is the same as the reflectance in the upper band, whether the surface is bare or covered with ice or water. A suitable reference band is centered at about 1.1 microns, which is lower than both the upper and lower bands. Accordingly, when light is reflected from an aluminum surface, if the intensity of light in the reference band is less than that of the upper band, then the rate of increase in reflectance may be determined and conventional trend removing techniques applied to remove the effect of this increasing reflectance with increasing wavelength prior to the determination of the contrast.

The graphs of FIGS. 2 to 4 assume a thin layer on the surface of about 2 millimeters. Since water and Type I and II fluids are liquids, layers of these substances do not exceed about this thickness. Ice could exceed this thickness, however, for thick layers of ice, the surface effect becomes insignificant in the face of the dominant effect of the ice. Should this occur, then the reflectance between the reference and upper bands would not increase even with a painted aluminum surface and there would be no need for, nor would there be, a correction in the intensity of the reflectance from the lower and upper bands.

Where the aluminum is painted other colours (black, blue, grey, green, red, yellow), again, the reflectance of the surface increases over the wavelengths of interest and this increase may be factored out with conventional detrending techniques.

Because the reflectance of unpainted aluminum is approximately constant over the wavelengths of interest, if an unpainted aluminum surface has no ice, water or Type I or II fluids on it, then the expected contrast would be approximately zero. Furthermore, for painted aluminum, after trend removal, if the surface has no ice, water or Type I or II fluids on it, the expected contrast would again be approximately zero. However, it has been observed that the detrended contrast for bare painted surfaces does have a small positive value, which value depends upon the colour. To compensate for this, the colour of the surface may be considered in deciding upon a threshold contrast which will be indicative of the presence of ice on a surface.

Figure 5:
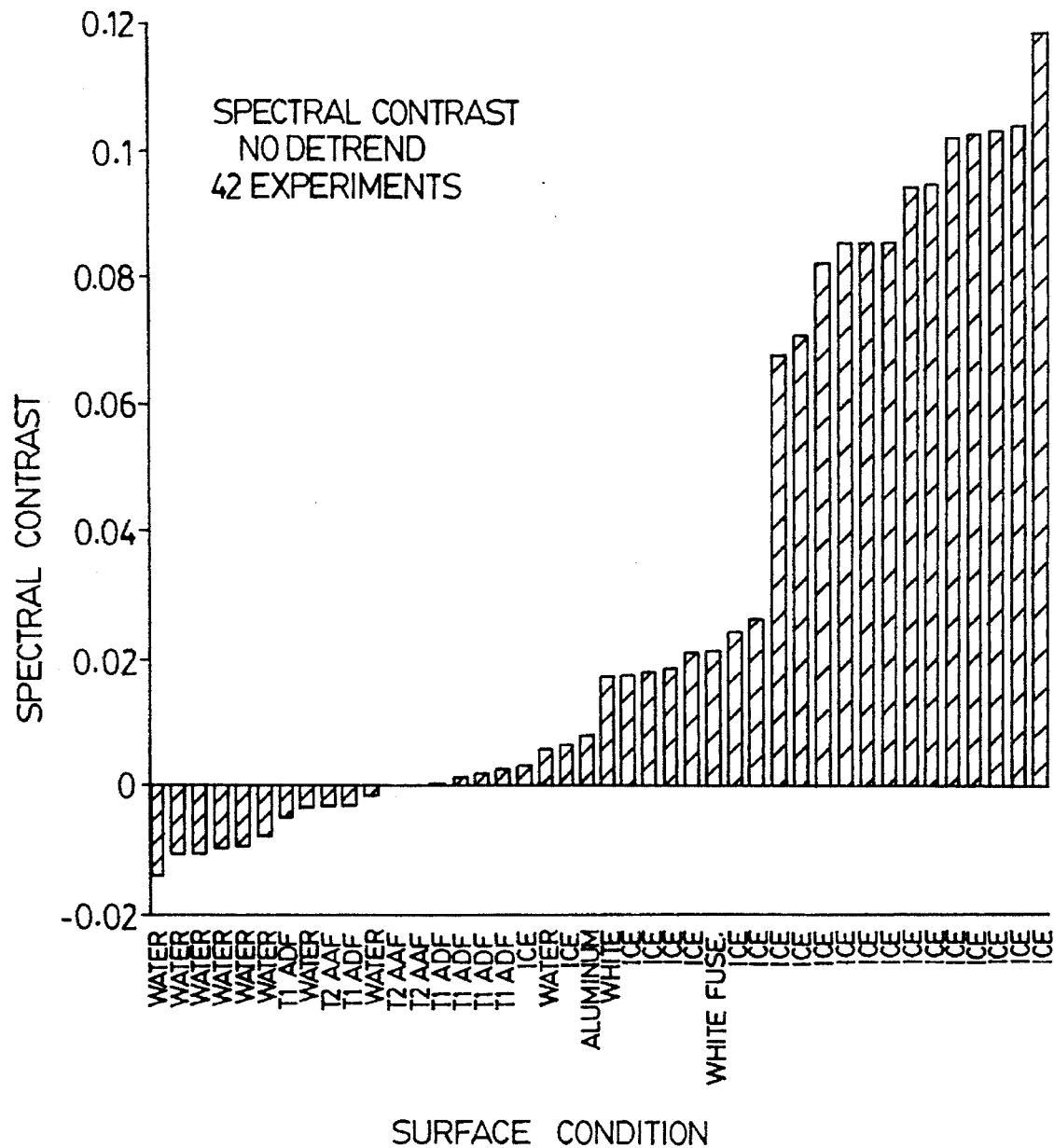
FIG. 5 is a bar graph illustrating the results of experiments utilizing the method of this invention.

FIG. 5 graphically presents a number of experiments in which the contrast was determined at an aluminum surface and a white painted aluminum surface under various conditions. No trend removal was made in these experiments. Where the surface was bare unpainted aluminum, it is referenced as "aluminum" on the graph. Bare white painted aluminum is referenced as "white". Aluminum, whether painted or not, when covered with water is designated "water". When the surface is covered with Type I aircraft de-icing fluid, it is designated "T1 ADF", when covered with Type II aircraft anti-icing fluid, it is designated "T2 AAF", and when covered with ice, it is designated "ice". The ice had varying thicknesses from experiment to experiment. From the graph, it will be apparent that when the contrast is negative, no ice is present on the surface. When it has a positive value above about 0.02, ice is certain to be present. When the value is between 0 and 0.02 ice is likely to be present. Trend removal would allow ice to be predicted with certainty for even lower positive contrast levels. While not apparent from the graph, the experiments also showed a monotonic increase in the contrast with increasing ice thickness.

Figure 6:
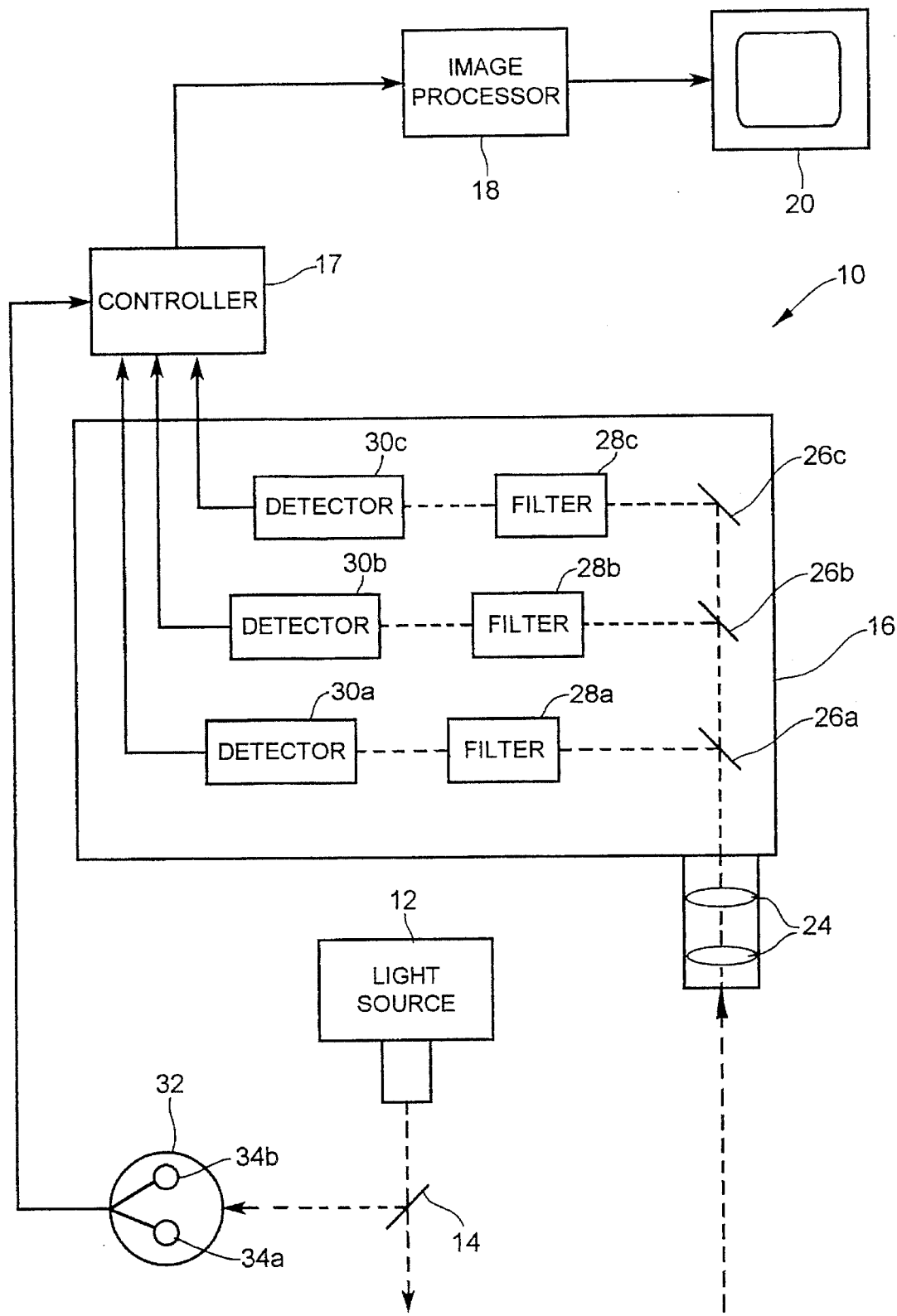
FIG. 6 is a schematic drawing of apparatus for determining the presence of ice on a surface made in accordance with this invention.

FIG. 6 illustrates apparatus for implementing the method of this invention. Turning to FIG. 6, apparatus 10 comprises a light source 12, a beam splitter 14, a multispectral camera indicated generally at 16, a controller 17, an image processor 18, an indicating display 20, and a light sensor 22. Camera 16 comprises lenses 24, beam splitters 26a, 26b, mirror 26c, optical bandpass filters 28a, 28b, 28c, and detector arrays 30a, 30b, 30c. Optical bandpass filter 28a passes light in the aforedescribed lower band, filter 28b passes light extending over the previously described upper band, and filter 28c passes light extending over the previously described reference band. The light sensor 22 comprises two light sensing elements 34a, 34b within a sphere 32 with a light diffusing surface of a material transparent to radiation with a wavelength of one to two microns. The sensing elements 34a, 34b are photodiodes with integral optical filters positioned to view the interior of the sphere. The optical filter of sensing element 34a passes light in the previously described lower band and the optical filter of element 34b passes light in the previously described upper band. Accordingly, the sensing elements measure the integrated intensity of the light incident on the sphere within these two bands. The light sensor is positioned to receive light from source 12 as well as ambient light. The output from the three detector arrays 30a, 30b, 30c, as well as the output from the sensing elements 34a, 34b of the light sensor 22, input controller 17. The controller outputs to a control input of light source 12 and to image processor 18.

In operation, apparatus 10 is positioned adjacent a surface to be investigated. The light sensor outputs a signal to controller 17 indicating the intensity of ambient light at the upper and lower wavelength bands. The controller activates light source 12 only if these intensity signals do not exceed a threshold.

Where the light source is off, ambient light will reflect from the surface into the lenses of camera 16. Where light source 12 is used, beam splitter 14 passes some of the light from the source to light sensor 22. The beam splitter reflects the remainder of the light so that it impinges upon the surface and reflected light from the surface enters the lenses 24 of camera 16. A one third portion of the light entering the camera is reflected by beam splitter 26a to pass through lower band filter 28a and impinge on detector array 30a. A further one third portion is reflected by beam splitter 26b to pass through upper band filter 28b and impinge on detector array 30b and the remaining one third portion is reflected by mirror 26c to pass through reference band filter 28c and impinge on detector array 30c. The intensity signals from the three detector arrays input controller 17. While signals are being received by the controller from the detector arrays 30a, 30b, 30c, the controller compares the intensity signals output by the two sensor elements 34a, 34b of the light sensor. If they are not the same, this means either the ambient light, or the light from the light source (possibly due to bulb aging) is not spectrally balanced at the wavelengths of interest. To compensate, the controller takes the ratio of the intensity signals from the sensor elements and applies this as a calibrating factor to the output of one of detector arrays 30a and 30b. The controller then outputs these signals, representative of the reflectance in the lower, upper, and reference bands, to the image processor 18. The processor 18 determines whether the intensity increases from the reference band signal to the upper band signal. If yes, the processor determines the rate of increase and utilizes this information to remove the effect from the lower and upper band signals. Next the processor determines the contrast as the difference in the intensities between the lower and upper band signals over the sum of the intensities of these band signals. The value of this contrast indicates whether or not there is ice on the surface. The computer then sends an appropriate input to display 20. Thereafter, apparatus 10 may be repositioned over another surface and the process repeated. In this way, apparatus 10 may be used to scan an aircraft surface. Areas of the surface found to be covered with ice may be sprayed with de-icing fluid and those areas then re-checked for ice.

Figure 7:
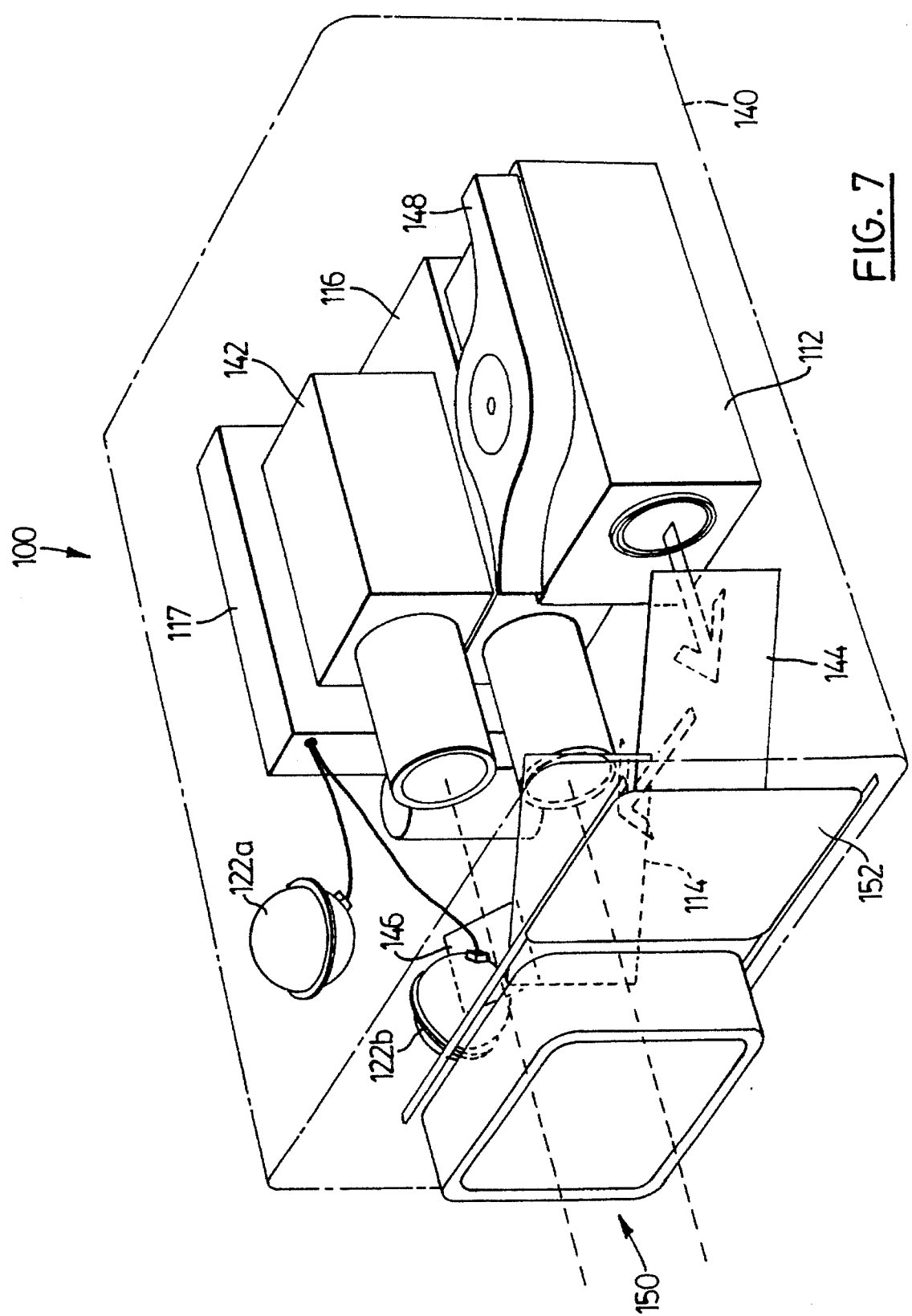
FIG. 7 is a perspective view of a portion of apparatus for determining the presence of ice on a surface, made in accordance with another aspect of this invention.

FIG. 7 is a perspective view of an apparatus 100 made in accordance with another aspect of this invention. Apparatus 100 comprises light source 112, a beam splitter 114, a multispectral camera 116, a controller 117, two light sensors 122a and 122b embedded in different sides of housing 140 (shown in phantom) so as to be orthogonal to the viewing axis of camera 116, a colour video camera 142, folding mirrors 144, 146, a cooling fan 148, a housing aperture 150, and an aperture door 152. Camera 116 is identical to camera 16 of FIG. 6 and each light sensor 122a, 122b is identical to light sensor 22 of FIG. 6. The controller 117 is designed to output to an image processor (not shown), which in turn would output to an indicating display (not shown).

The exterior hemisphere of each of the two light sensors 122a, 122b is exposed to ambient light. Because these sensors are positioned on different sides of housing 140, at least one should be exposed to the sky regardless of the orientation of housing 140. When the apparatus 100 is to be used, door 152 covering aperture 150 is opened. Based on ambient light conditions sensed by the light sensors, controller 117 decides whether to activate light source 112. Folding mirror 144 is provided to redirect light from light source 122 toward beamsplitter 114. The beamsplitter redirects some light from the source 112 to the surface under investigation and passes the remainder to folding mirror 146, which redirects this light to light sensor 122a. Light reflected from the surface under investigation passes not only to multispectral camera 116 but also to colour video camera 142. The controller 117 is input with the bandpass signals from the multispectral camera, the signals from the light sensors 122a, 122b, and, as well, the signal from the video camera. The controller uses the light sensor signals to calibrate the upper and lower bandpass signals and then passes the calibrated signals, along with the reference band signal and video camera signal to the image processor.

The image processor performs detrending calculations to compensate for painted surfaces and calculates contrasts. In addition, from the video signal, the processor determines the colour of the surface. The colour determination is applied to a look up table which returns a threshold contrast for indicating the presence of ice. The processor passes the contrasts, the determined colour, the threshold contrast, and the video signal to the display. The video signal allows an operator to view the surface and the operator is also able to note whether the contrast is indicative of the presence of ice in order to take appropriate action.

It has been found that the apparatus of the subject invention will provide reliable results for angles of incidence up to about seventy degrees. This is due to the fact that the apparatus of this invention determines the presence or absence of ice utilizing relative intensities (in calculating the contrast).

The multispectral camera (16 of FIG. 6 or 116 of FIG. 7) may be modified to include a filter wheel between the camera lens and a single detector array. The filter wheel would then be controlled to sequentially interject a low bandpass filter, a high bandpass filter, and a reference filter in the light path from the camera lens. In this way the single detector array would sequentially measure the intensity of light in the low band, the high band, and the reference band and pass corresponding intensity signals sequentially to the controller of the camera. The controller would process these signals as before.

Other modifications will be apparent to those skilled in the art and, therefore, the invention is defined in the claims.

What is claimed is:

1. A method of indicating the presence of ice on a surface, comprising the following steps:
   detecting the intensity of reflected light from said surface at a first lower wavelength band, said lower band being within a band extending from about 1.1 microns to about 1.3 microns;
   detecting the intensity of reflected light from said surface at a second upper wavelength band having substantially the same bandwidth as said lower band, said upper band being within a band extending from about 1.16 microns to about 1.3 microns; and
   determining the presence or absence of ice on said surface based upon the intensity of reflected light at said first band and the intensity of reflected light at said second band.

2. A method of indicating the presence of ice on an aircraft surface, comprising the following steps:
   detecting the intensity of reflected light from said surface at a first lower wavelength band, said lower band being within a band extending from about 1.16 microns to about 1.24 microns;
   detecting the intensity of reflected light from said surface at a second upper wavelength band having substantially the same bandwidth as said lower band, said upper band being within a band extending from about 1.24 microns to about 1.29 microns; and
   determining the presence or absence of ice on said surface based upon the intensity of reflected light at said first band and the intensity of reflected light at said second band.

3. The method of claim 2 wherein said lower band is within a band extending from about 1.16 to about 1.20 microns and said upper band is within a band extending from about 1.24 to 1.28 microns.

4. The method of claim 3 including the step of indicating in response to said determining step.

5. The method of claim 4 wherein said determining step includes comparing said lower band intensity with said upper band intensity.

6. The method of claim 4 wherein said determining step includes determining the ratio of the difference of the lower band intensity and the upper band intensity to the sum of the lower band intensity and the upper band intensity.

7. The method of claim 6 including the step of detecting the intensity of reflected light from said surface at a third reference wavelength band having substantially the same bandwidth as said upper band and centered at about 1.1 microns and wherein said determining step is also based upon the intensity of reflected light from said reference band.

8. The method of claim 7 wherein said determining step comprises reducing the detected intensity at one of said lower band and said upper band by an amount based upon the intensity increase between said reference band and said upper band, if any, prior to determining said ratio.

9. The method of claim 8 including the step of sensing the intensity of light incident on said surface at said lower band and said upper band and wherein said determining step is also based upon any difference in intensity of sensed incident light at said lower band and said upper band.

10. The method of claim 4 including the step of sensing the intensity of light incident on said surface at said lower band and said upper band and wherein said determining step is also based upon any difference in intensity of sensed incident light at said lower band and said upper band.

11. The method of claim 10 including the step of determining the color of said surface and wherein said determining step is also based upon said color determination.

12. The method of claim 4 including the step of determining the color of said surface and wherein said determining step is also based upon said color determination.

13. The method of claim 4 including the step of illuminating said surface where the sensed intensity of light incident on said surface at said lower band and said upper band falls below a predetermined level.

14. Apparatus for determining the presence of ice on a surface, comprising the following:
   bandpass filter means configured to pass light within a first lower wavelength band, said lower band being within a band extending from about 1.1 microns to about 1.3 microns and within a second upper wavelength band having substantially the same bandwidth as said lower band, said upper band being within a band extending from about 1.16 microns to about 1.3 microns, said bandpass filter means for receiving light reflected from said surface;
   means for detecting the intensity of light passed through said bandpass filter means; and
   means responsive to said detecting means for determining the presence or absence of ice on said surface.

15. The apparatus of claim 14 wherein said filter means is configured to pass light within a lower band being within a band extending from about 1.16 to about 1.20 microns and within an upper band being within a band extending from about 1.24 to 1.28 microns.

16. The apparatus of claim 15 wherein said determining means includes means for determining the ratio of the difference of the lower band intensity and the upper band intensity to the sum of the lower band intensity and the upper band intensity.

17. The apparatus of claim 16 including indicating means responsive to said determining means.

18. The apparatus of claim 16 including means to sense the intensity of light incident upon said surface at said lower band and at said upper band and wherein said determining means is responsive to said incident light sensing means.

19. The apparatus of claim 18 including a source of light for illuminating said surface, said light source being responsive to said incident light sensing means.

20. The apparatus of claim 19 wherein said bandpass filter means passes light at a third reference wavelength band having substantially the same bandwidth as said upper band and centered at about 1.1 microns.

21. The apparatus of claim 20 wherein said determining means comprises means to reduce the detected intensity of one of said lower band and said upper band by an amount based upon the intensity increase between said reference band and said upper band, if any, said ratio determining means being responsive to said intensity reducing means.

22. The apparatus of claim 21 wherein said bandpass filter means comprises a lower bandpass filter, an upper bandpass filter, and a reference bandpass filter, said detecting means comprises a light detector positioned to receive light filtered by said lower bandpass filter, a second light detector positioned to receive light filtered by said upper bandpass filter, and a third light detector positioned to receive light filtered by said reference bandpass filter, said determining means comprises a processor, and said incident light sensing means comprises a light sensor.

23. The apparatus of claim 16 including a video camera for receiving light reflected from said surface, said determining means being responsive to output signals from said video camera.

24. The apparatus of claim 14 wherein said bandpass filter means comprises a lower bandpass filter and an upper bandpass filter, said detecting means comprises a light detector positioned to receive light filtered by said lower bandpass filter and a second light detector positioned to receive light filtered by said upper bandpass filter, and said determining means comprises a processor.

* * * * *